(12) United States Patent
Gharibi Loron

(10) Patent No.: US 10,098,626 B2
(45) Date of Patent: Oct. 16, 2018

(54) HYDRAULIC ANNULAR SURGICAL RETRACTOR

(71) Applicant: Ali Gharibi Loron, Ardabil (IR)

(72) Inventor: Ali Gharibi Loron, Ardabil (IR)

( * ) Notice: Subject to any disclaimer, the term of this patent is extended or adjusted under 35 U.S.C. 154(b) by 40 days.

(21) Appl. No.: 15/226,901

(22) Filed: Aug. 2, 2016

(65) Prior Publication Data
US 2018/0035994 A1    Feb. 8, 2018

(51) Int. Cl.
*A61B 1/32* (2006.01)
*A61B 17/02* (2006.01)
*A61B 90/30* (2016.01)
*A61B 17/00* (2006.01)

(52) U.S. Cl.
CPC .......... *A61B 17/0293* (2013.01); *A61B 17/02* (2013.01); *A61B 90/30* (2016.02); *A61B 2017/00946* (2013.01); *A61B 2017/00991* (2013.01); *A61B 2560/04* (2013.01)

(58) Field of Classification Search
CPC . A61B 17/02; A61B 17/0293; A61B 17/3439; A61B 17/3423; A61B 17/3431; A61B 2017/0255; A61B 2017/00991; A61B 2017/3429; A61B 2017/3433; A61B 2017/3435
See application file for complete search history.

(56) References Cited

U.S. PATENT DOCUMENTS

| | | | | |
|---|---|---|---|---|
| 3,863,639 | A | * | 2/1975 | Kleaveland ........ A61B 17/0293 128/850 |
| 4,447,227 | A | | 5/1984 | Kotsanis |
| 4,488,523 | A | | 12/1984 | Shichman |
| 4,850,957 | A | | 7/1989 | Summers |
| 5,337,754 | A | | 8/1994 | Heaven |
| 5,339,723 | A | | 8/1994 | Huitema |
| 5,342,385 | A | * | 8/1994 | Norelli ................. A61B 17/02 604/104 |
| 6,190,312 | B1 | | 2/2001 | Fowler, Jr. |
| 6,416,470 | B2 | | 7/2002 | Paolitto |
| 7,041,056 | B2 | * | 5/2006 | Deslauriers ............ A61B 1/32 600/208 |
| 9,357,910 | B2 | * | 6/2016 | Smith ..................... A61B 1/24 |
| 9,668,721 | B2 | * | 6/2017 | Smith ..................... A61B 1/24 |
| 9,743,954 | B2 | * | 8/2017 | Albrecht ........... A61B 17/0218 |
| 2002/0111537 | A1 | | 3/2002 | Taylor |
| 2003/0208223 | A1 | * | 11/2003 | Kleiner ............. A61B 1/00151 606/198 |
| 2012/0245425 | A1 | * | 9/2012 | Okoniewski ....... A61B 17/3423 600/207 |
| 2013/0137932 | A1 | * | 5/2013 | Piech ...................... A61B 1/32 600/204 |
| 2013/0178709 | A1 | * | 7/2013 | Suh .................... A61B 17/0293 600/205 |

(Continued)

*Primary Examiner* — Jacqueline Johanas
(74) *Attorney, Agent, or Firm* — NovoTechIP International PLLC

(57) ABSTRACT

A segmented annular tube is formed of a flexible material and includes an intussuscepted tube segment. The intussuscepted tube segment includes a core tube having a sheathed telescoping portion, surrounded by an inwardly folded sheathing portion of an outer tube. A pump selectively urges a fluid the segmented annular tube. Upon a fluid pressure, the folded sheathing portion unfolds and telescopes the core tube, expanding the segmented annular tube.

19 Claims, 11 Drawing Sheets

(56) References Cited

U.S. PATENT DOCUMENTS

| | | | |
|---|---|---|---|
| 2013/0184535 A1* | 7/2013 | Suh | A61B 17/0293 |
| | | | 600/210 |
| 2014/0100430 A1* | 4/2014 | Beane | A61B 17/11 |
| | | | 600/207 |
| 2015/0112147 A1* | 4/2015 | Okoniewski | A61B 17/3423 |
| | | | 600/207 |
| 2016/0074064 A1* | 3/2016 | Okoniewski | A61B 17/3423 |
| | | | 600/204 |
| 2016/0278759 A1* | 9/2016 | Smith | A61B 1/24 |
| 2016/0287240 A1* | 10/2016 | Suh | A61B 17/0293 |
| 2017/0128059 A1* | 5/2017 | Coe | A61B 17/0218 |

* cited by examiner

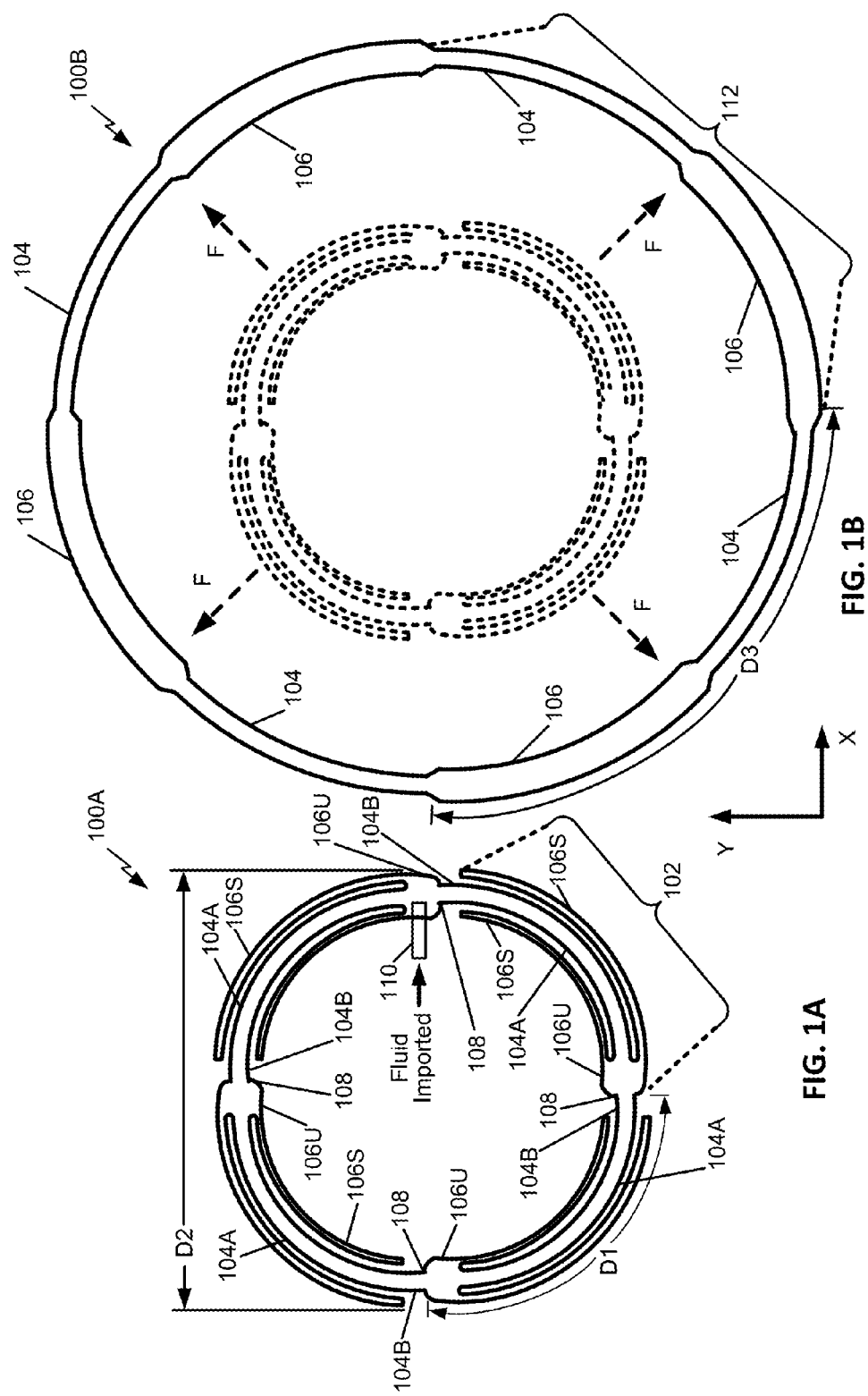

HYDRAULIC ANNULAR SURGICAL RETRACTOR

TECHNICAL FIELD

The present application generally relates to surgical retractors and relates more particularly to an improved retractor comprised of flexible material which can be applied in a contracted state and then fluidly pressurized with a fluid to achieve rigidity and thereby retraction of tissue.

BACKGROUND

Conventional retractors, used in surgical procedures of the abdomen, thorax, vagina, etc., often utilize rigid or semi-malleable metallic retractors applied to influence the position of tissues within and adjacent to the operative field. These conventional retractors are available in a plurality of sizes, shapes, and configurations, but a common feature is rigidity of the basic materials of construction. A problem with rigid retractors is that their unyielding nature can have untoward effects, such as neuronal impingement, pressure necrosis of soft tissue, incomplete hemostasis requiring additional efforts to achieve hemostasis (e.g., electric cautery), asymmetric retraction of soft tissue. Some of these can have secondary effects. For example, neuronal impingement from conventional retractors can result in transient or residual deficits. Another shortcoming of conventional retractors is the need for a surgical assistant to physically hold the retractor by hand and thereby apply the tissue retracting force.

Attempts to overcome these problems include increasing the retractor-tissue interface areas and introducing a curvature to the retractor blade. However, in practicality, the lateral edges of the rigid retractor blade still present a localized focus of high pressure against soft tissue. Also, specific locations of the underlying sensitive structures, such as nerve fibers and blood vessels and lymphatic channels, are subject to extensive anatomic variation. The surgeon must therefore exercise the judgment and wisdom of experience to arrive at a "best-guess" location for application of the retractor blade to preferably avoid compression of these structures.

The above-identified attempts to solve or reduce problems such as neuronal impingement, pressure necrosis of soft tissue, incomplete hemostasis, and asymmetric retraction of soft tissue, in addition to being unsatisfactory for certain applications, do not remove the requirement for a surgical assistant to hold the retractor. The requirement for a surgical assistant can introduce additional problems. For example, the assistant may become fatigued. In addition, the assistant has a different perspective than the primary operation, i.e., the surgeon, and may therefore inaccurately place the retractor. Also, the assistant may have suboptimum exposure within the operative field.

Attempts to eliminate the need for a surgical assistant include rigid or malleable metallic retractor blades attached to self-retaining retraction frames. The blades can be connected to surgical table accessories or to flexible/lockable retraction arms. However, although such retractors can be partially or totally within the sterile operative field, they extend well beyond the general dimension of the incision site. This can cause a reduction in the surgeon's access to the operative site due to interference by the external frameworks. Also, the frameworks can potentially obstruct the surgeon's vision, for example, when intra-operative complications necessitate a change in surgical approach. IN addition, the ultimate tissue retraction is still achieved by means of rigid or malleable metallic retractor blades, thereby inducing the previously mentioned problems with hemostasis, necrosis, neuronal impingement, etc.

Therefore, a need exists for a tissue retractor that eliminates, or at least significantly reduces retractor-related problems such as, but not limited to, the examples described above.

SUMMARY

Disclosed aspects include fluidly expandable surgical retractor that can include a segmented annular tube, formed of a flexible material and including an intussuscepted tube segment; a feed tube in fluid communication with an interior of the annular tube, and a pump, having an output coupled to the feed tube, and having an input configured to receive a liquid. In an aspect, the fluidly expandable surgical retractor can further include a flow control valve, configured to selectively increase and decrease a flow of the fluid through the feed tube, into and out of the annular tube. In another aspect, the intussuscepted tube segment can be configured to expand and retract in association with increase and decrease, respectively, of the flow of the fluid through the feed tube.

Additional features can include, for example, the flow control valve can be a manually actuated valve.

In an aspect, the intussuscepted tube segment can be configured to have a resting mode in response to less than a first pressure of the fluid, and a fully expanded mode in response to above a second pressure of the fluid. Features can include, in the resting mode, the intussuscepted tube segment including a core tube having a sheathed telescoping portion, configured as pulled into and surrounded by an inwardly folded sheathing portion of an outer tube. In an implementation the inwardly folded sheathing portion of the outer tube can have a length.

In an aspect, the inwardly folded sheathing portion of the outer tube can be configured to unfold and telescope the core tube in response to an increase in the pressure of the fluid from less than the first pressure to greater than the second pressure. In another aspect, the inwardly folded sheathing portion of the outer tube can be configured to unfold and telescope the core tube, in a direction corresponding to a direction of the fluid pressure, to a distance approximately equal to the length of the inwardly folded sheathing portion in the resting mode.

In one aspect, the segmented annular tube can include an upper telescoping tube segment and lower upper telescoping tube segment, in fluid connection through a first coupling and a second coupling to form the annular multi-segmented tube. Example features of the upper telescoping tube segment can include an upper core tube, which can include an unsheathed center portion, a sheathed left portion, and a sheathed right portion. Features can include a first inwardly folded sheath that extends from the first coupling approximately 90 degrees in a clockwise direction, to a terminating end, and a second inwardly folded sheath that can extends from the second coupling, approximately 90 degrees in a counter-clockwise direction, to a terminating end that is spaced by a gap from the terminating end of the first inwardly folded sheath.

In another aspect, the segmented annular tube can include a plurality of intussuscepted tube segments, and each intussuscepted tube segment can include a corresponding core tube having a corresponding sheathed telescoping portion, pulled into and surrounded by a corresponding inwardly folded sheathing portion of a corresponding outer tube. In one implementation, the segmented annular tube can be approximately circular in the resting mode, and the plurality of intussuscepted tube segments can be arranged such that, in response to the corresponding inwardly folded sheathing portion of each intussuscepted tube segment unfolding and telescoping the core tube, the segmented annular tube can expand radially, at a substantially uniform rate. In another implementation, the plurality of intussuscepted tube segments can be arranged such that, in response to the corresponding inwardly folded sheathing portion of each intussuscepted tube segment unfolding and telescoping the core tube, the segmented annular tube expands to an elliptical perimeter. In yet another implementation, the plurality of intussuscepted tube segments can be arranged such that, in response to the corresponding inwardly folded sheathing portion of each intussuscepted tube segment unfolding and telescoping the core tube, the segmented annular tube expands in a directionally biased manner.

One or more implementations of a fluidly expandable surgical retractor according to various aspects can include a light source, a power source, or both. In one implementation, the pump can be a hydraulic pump.

Implementations can also include a plurality of bracings, each of the bracings being a hollow tube, and each of the bracing extending between and providing a fluid communication between the first annular tube and the second annular tube. Furthermore, each bracing may be an intussuscepted tube or a hollow tube. In addition, the first and second segmented annular tubes, and the plurality of bracings can be configured as scaffolding that, upon an increase in flow rate of the fluid through the feed tube, expands outwardly. Furthermore, each annular tube may be loaded separately by individual fluid connectors.

Example implementations also include a fluidly-expandable surgical device, that can include a hollow member formed of an inner C layer, and outer C layer, and a fluid-tight passage between the inner C layer and the outer C layer, and a fluid supply, configured to supply a fluid, at a selectable flow rate into and out from the fluid-tight passage between the inner C layer and the outer C layer. In an aspect, the inner C-shaped layer can be thicker than the outer C-shaped layer, by a difference such that upon an increase of the flow rate into and out from the fluid-tight passage, the inner C layer is urged in a clamping direction.

Exemplary methods are disclosed, including a method for retracting tissue, which can include placing into a surgical site a segmented annular tube, comprising a flexible material and including an intussuscepted tube segment, the intussuscepted tube segment including a core tube having a sheathed telescoping portion, configured as pulled into and surrounded by an inwardly folded sheathing portion of an outer tube, and importing a fluid into the segmented annular tube, at a pressure that cases the inwardly folded sheathing portion of the outer tube to unfold and telescope the core tube to expand the segmented annular tube.

Additional details of the present application are set forth in the accompanying drawings and the description below. Once the details of the application are known, additional alternatives and changes will become obvious to one skilled in the art.

As will be understood and appreciated by persons of ordinary skill upon reading this disclosure, features and advantages of fluidly expandable retractors according to described concepts can include, but are not limited to, an ability to form the apparatus from materials that are less expensive and more widely available, and with a structure that is more easily mass produced. Additional advantages can include, but are not limited to, a more flexible generic design, or at least a much smaller set of variations needed to apply to a wide range of surgical procedures. Advantages can also include an ease of including additional functionality, for example, an internal cavity retractor with incorporated pouch to accept mobile organs such as bowel or momentum to protect against desiccation. Still further advantages can include, without limitation, a cost-effective disposable retractor, which can avoid the expense of sterilization and/or the risks of faulty sterilization. Advantages can include, in addition, a retractor that can provide a substantially larger contact with the incision site. In addition, features and advantages can include application, and use by a sole operator, e.g., a surgeon without an assistant. Advantages can include, in addition, a small retractor in body tubes such as coronary arteries for expansion of the narrow structures.

BRIEF DESCRIPTION OF THE DRAWINGS

Features of the subject technology are set forth in the appended claims. However, for purpose of explanation, several implementations of the subject technology are set forth in the following figures.

FIGS. 1A and 1B illustrate, respectively, a rest mode and a fully expanded mode of one example four-segment intussuscepted tube hydraulic surgical retractor according to one or more aspects.

DETAILED DESCRIPTION

Figure 2A:
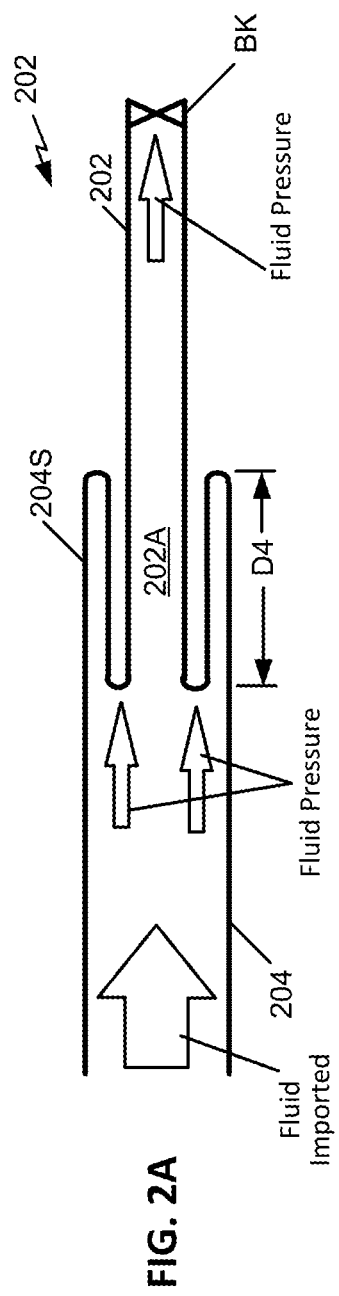
FIGS. 2A, 2B, and 2C illustrate, respectively, a rest mode, a partially extended mode, and a fully extended mode of one exemplary intussuscepted tube segment of an intussuscepted tube hydraulic surgical retractor according to one or more aspects.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

FIGS. 1A and 1B illustrate, respectively, a rest mode and a fully expanded mode of one four-segment example of a multi-segment intussuscepted tube hydraulic surgical retractor according to one or more aspects.

Referring to FIG. 1A, the example multi-segment intussuscepted tube hydraulic surgical retractor, in rest mode, can include a segmented annular tube 100 that includes a concatenation of four intussuscepted tube arc segments. A representative one of the four is labeled as 102. Each of the four intussuscepted tube arc segments 102 can include a core tube (shown extended as structure 104 in FIG. 1B) having in its FIG. 1A mode a sheathed telescoping portion 104A and an unsheathed distal portion 104B. The sheathed telescoping portion 104A can have an arrangement that can appear pulled into or taken into, and surrounded by an inwardly folded sheathing portion 106S of an outer tube (shown extended as structure 106 in FIG. 1B). The unsheathed distal portion 104B of the core tube 104 can connect at connection 108 to an unfolded portion 106U of a succeeding (in a counter-clockwise direction) intussuscepted tube arc segment 102. Example materials for the intussuscepted tube arc segments 102 can include, without limitation, natural latex rubber, polyurethane, silicone, polyolefin, and polyethylene.

For purposes of description, the arc length D1 of each of the four intussuscepted tube arc segments 102 will be in reference to the arc length from one connection 108 to the next connection 108. This is only for purposes of description, as persons of ordinary skill, upon reading this disclosure, can identify alternative reference points for measuring arc length.

Referring to FIG. 1A, the four-segment example of a multi-segment intussuscepted tube hydraulic surgical retractor, in rest mode, can have an outer diameter D2. In an aspect, a fluid ingress/egress port 110 can receive a fluid from an external source (not visible in FIG. 1A), at a pressure that can be controlled, for example, by a surgeon, as described in greater detail later in this disclosure. In response to the pressure, the sheathed telescoping portion 104A of each intussuscepted tube arc segment 102 can telescope to a fully extended position, which transforms the intussuscepted tube arc segment 102 to a fully extended tube arc segment 112, which is illustrated in FIG. 1B. This causes an outer perimeter (visible in FIGS. 1A and 1B, but not separately numbered) of the segmented annular tube 100 to expand radially outward. The radial expansion exerts forces such as represented by the labeled force vectors "F. The result is the fully expanded mode segmented annular tube 100".

Comparing FIGS. 1A and 1B, it is seen that the FIG. 1B fully extended mode annular tube 100' provides, through novel intussuscepted tube aspects disclosed herein, a wide diameter inner perimeter (visible, but not separately numbered), establishing a large, unobstructed operation field for the surgeon. Persons of ordinary skill will appreciate this feature as adding significant value to increasing the outer perimeter alone.

Figure 2B:
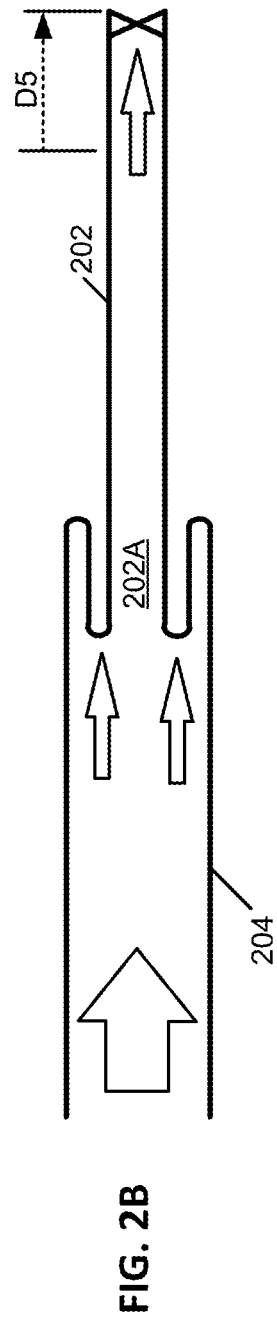
Figure 2C:
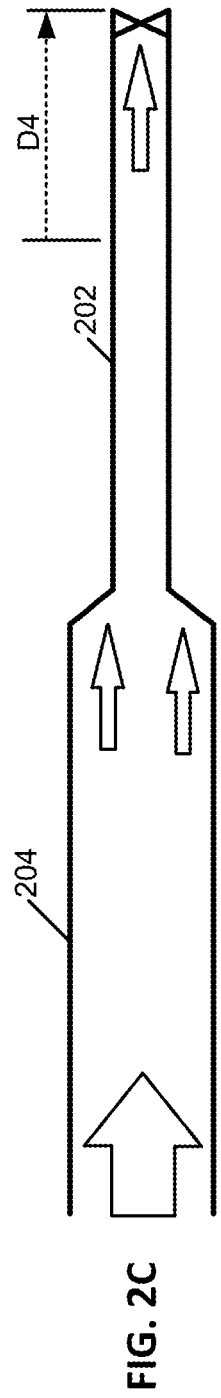

Aspects by which the intussuscepted tube arc segments 102 telescope out to the fully extended position, to transform to the fully extended tube arc segments 112 are described in greater detail in reference to FIGS. 2A-2C. Additional structures and configurations are described in reference to FIGS. 6A-6C and FIGS. 7A-7C.

The arc length D3 of each fully extended tube arc segment 112 is the sum of the arc length (visible in FIG. 1A but not separately numbered) of the sheathed telescoping portion 104A of the core tube 104 and the arc length (visible in FIG. 1A but not separately numbered) of the surrounding inwardly folded sheathing portion 106S of the outer tube 106. In the FIG. 1A example the arc length of the sheathed telescoping portion 104A of the core tube 104 is approximately the same as the arc length of the surrounding inwardly folded sheathing portion 106S of the outer tube 106. Therefore, in this example, D3 can be approximately thrice D1. Accordingly, the outer diameter (visible in FIG. 1B but not separately labeled) of the fully expanded segmented annular tube 100', for this example, is approximately thrice the diameter D2 of the rest mode segmented annular tube 100.

The rest mode annular tube 100 of FIG. 1A is formed of four intussuscepted tube arc segments 102, and each of the four intussuscepted tube arc segments 102 is similarly configured. Therefore, the forces F are substantially uniform. In other words, the outer perimeter of the annular tube 100 expands the same amount along the horizontal, or "X" axis, as along the vertical or "Y" axis. Also, the expansion is substantially symmetrical (i.e., equal in the left and right directions along the X axis, and equal in the up and down directions along the Y axis, relative to the viewing plane of FIGS. 1A and 1B). As described in greater detail later in this disclosure, one alternative implementation of a multi-segment intussuscepted tube hydraulic surgical retractor according to one or more aspects can be configured to expand along only one of the X axis and Y axis. As also described in greater detail later in this disclosure, another alternative implementation of a multi-segment intussuscepted tube hydraulic surgical retractor according to one or more aspects can be configured to expand asymmetrically, e.g., to expand substantially more in one direction than other along the "X" axis, or along the "Y" axis.

Referring to FIGS. 2A-2C, an example mechanism of an intussuscepted tube segment telescoping upon fluid pressure will be described. The example intussuscepted tube segment in FIGS. 2A-2C is shown, for purposes of description, as extending along a linear axis. The illustrated example intussuscepted tube segment, though, is flexible can be arced to implement one of the intussuscepted tube arc segments 102 of FIG. 1A.

FIG. 2A illustrates a rest mode of an intussuscepted tube segment, having a sheathed portion 202A, arranged as pulled or taken into, and surrounded by an inwardly folded sheathing portion 204S of an outer tube 204.

FIG. 2B shows a partially extended mode, resulting from a particular pressure level of the imported fluid. To simulate pressure that would result from importation of fluid into a closed loop concatenation of, for example, four rest mode intussuscepted tube segments 202, an artificial obstruction BK is placed at the distal end (visible in FIGS. 2A-2C) but not separately labeled) of the telescoping core tube 202. A mechanism for a surgeon or other user to control the pressure is described in greater detail later in this disclosure. The sheathed portion 202A of the telescoping core tube 202 has a length D4.

Referring to FIG. 2B, in the partially extended mode the telescoping core tube 202 has telescoped a distance D5 in the direction of the fluid pressure. The distance D5 is less than D4 because, being partially extended, there is a remaining sheathed portion 202A".

FIG. 2C shows a fully extended mode, resulting from another pressure level of the imported fluid, higher than the pressure level that produced the FIG. 2B partially extended mode. In the FIG. 2C fully extended mode, the telescoping core tube 202 has telescoped a total extension distance D4—which is the length of the sheathed portion 202A of the telescoping core tube 202 in the FIG. 2A resting mode.

Figure 3:
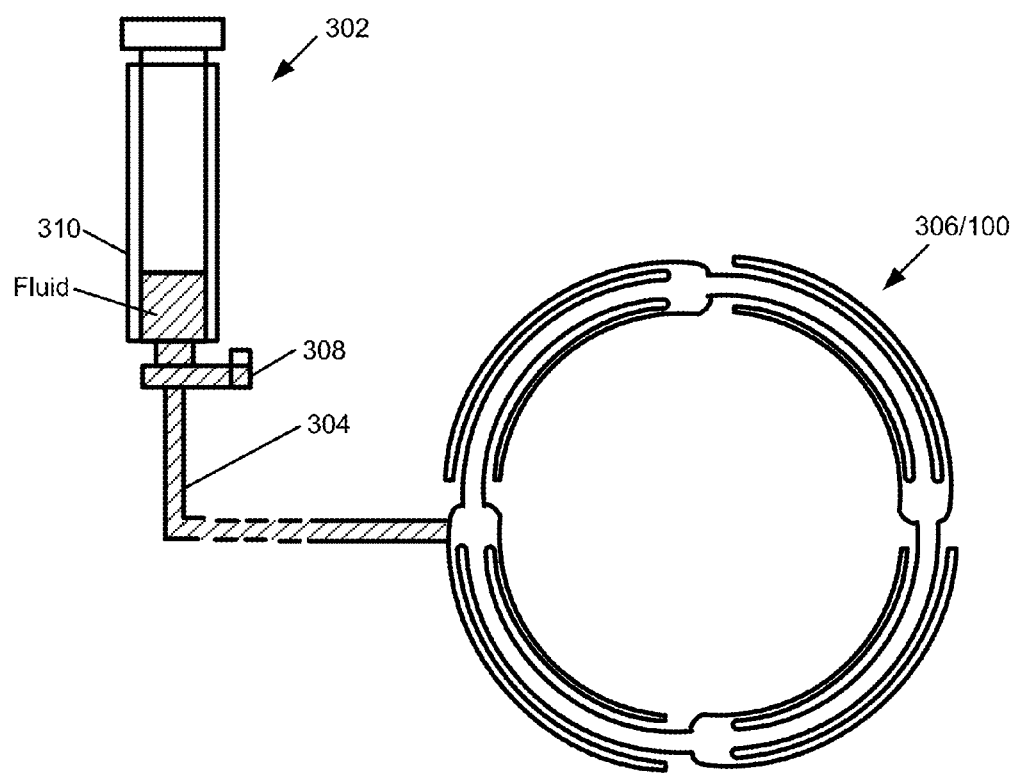
FIG. 3 illustrates one exemplary manual plunger actuated intussuscepted tube hydraulic surgical retractor, with a pressure control valve, according to one or more aspects.

FIG. 3 illustrates one exemplary hand actuated intussuscepted tube hydraulic surgical retractor 300, with a pressure control valve, according to one or more aspects. Referring to FIG. 3, the hand actuated intussuscepted tube hydraulic surgical retractor 300 can include a hand pump 302 configured to urge, under the control of a surgeon or other user, a fluid through a feed tube 304 and into a multi-segment intussuscepted tube hydraulic surgical retractor 306 according to one or more aspects. For illustration, FIG. 3 the shows the multi-segment intussuscepted tube hydraulic surgical retractor 306 implemented as the four-segment intussuscepted tube hydraulic surgical retractor 100 illustrated in FIGS. 1A-1B. It will be understood that the four-segment intussuscepted tube hydraulic surgical retractor example 100 is only for purposes of example, and that the multi-segment intussuscepted tube hydraulic surgical retractor 306 can be implemented, for example, according to the FIG. 4 configuration, or the FIG. 5 configuration, or any variation of either, or any other configuration of an annular tube comprising one or more intussuscepted tube segments according to concepts disclosed herein.

Referring to FIG. 3, the hand actuated intussuscepted tube hydraulic surgical retractor 300 can include a valve 308 and a fluid container 310. In an example operation, the surgeon or other user may use the hand pump 302 to discharge the fluid from the fluid container 310, through the feed tube 304 into the multi-segment intussuscepted tube hydraulic surgical retractor 306. The valve 308 can be manually adjustable to vary the flow rate of the fluid into and out of the multi-segment intussuscepted tube hydraulic surgical retractor 306. The fluid flow through feed tube 304 can provide controllable, selectable expansion of the multi-segment intussuscepted tube hydraulic surgical retractor 306 within the surgical site. The expansion may be controlled by the surgeon and can cause the surgical site to retract. As a result, the surgeon has more access to the surgical site, or the wound.

In one implementation, based on the size and depth of the surgical site, the hydraulic surgical retractor may use a hydraulic pump (not visible in the figures) to provide large amounts of fluids. In another implementation, based on the depth of the surgical site and the surgeon need, a light source may also be used. A power source may be used to provide the light source with the power necessary to operate.

Figure 4:
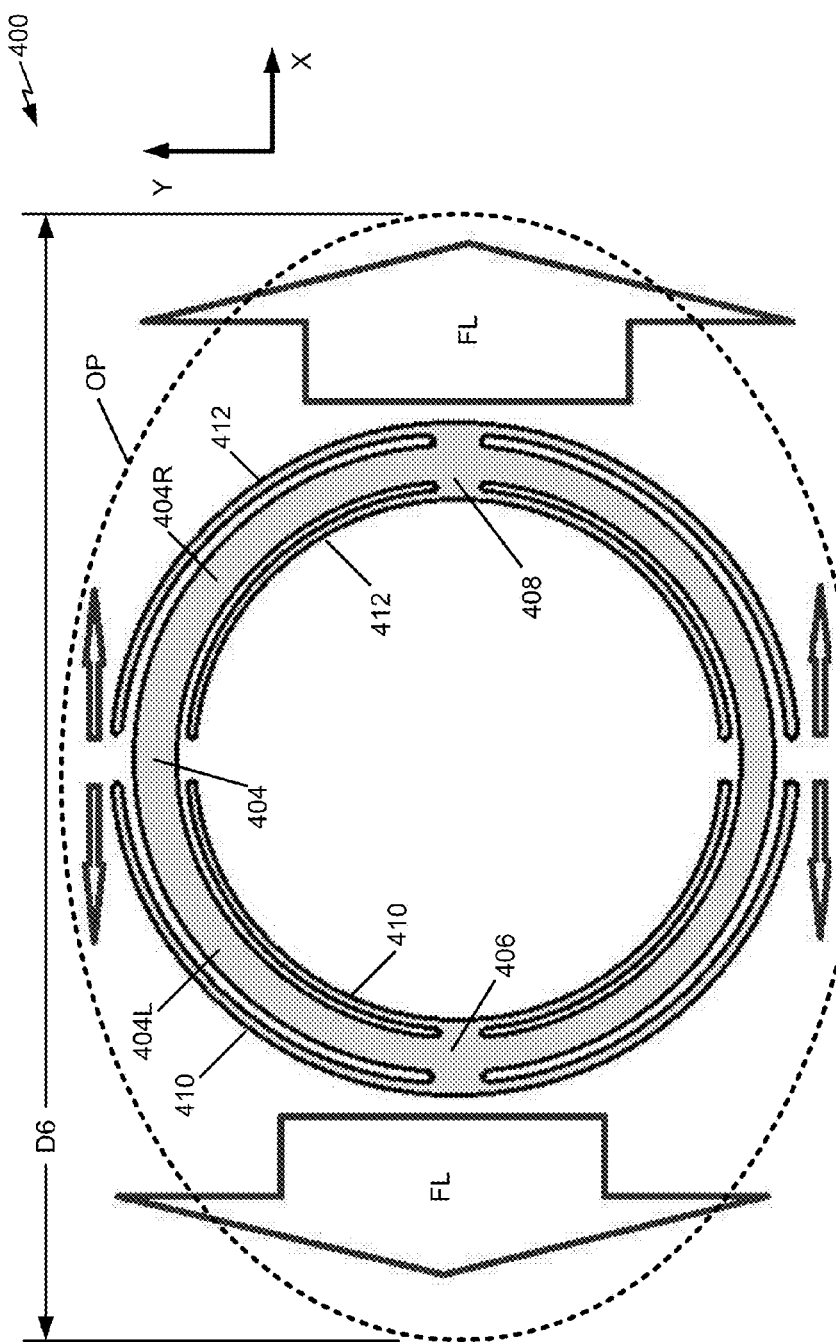
FIG. 4 illustrates a rest mode, and a diagrammed expansion, of one example elliptically expanding multi-segment intussuscepted tube hydraulic surgical retractor according to one or more aspects.

FIG. 4 illustrates a rest mode, and a diagrammed expansion, of one example elliptically expanding multi-segment intussuscepted tube hydraulic surgical retractor 400 according to one or more aspects. Referring to FIG. 4, the elliptically expanding multi-segment intussuscepted tube hydraulic surgical retractor 400 can include an upper telescoping tube segment 402 that can include an upper core tube 404. The upper core tube 404 can have an unsheathed center portion 404A, a sheathed left portion 404L and a sheathed right portion 404R. The elliptically expanding multi-segment intussuscepted tube hydraulic surgical retractor 400 can include a lower telescoping tube segment (visible in FIG. 4, but not separately labeled), which can be structured identically to the upper telescoping tube segment 402. The upper telescoping tube segment 402 and lower telescoping tube segment can be in fluid connection through a first coupling 406 and a second coupling 408 to form an annular multi-segmented tube (visible in FIG. 4, but not separately labeled).

Referring to FIG. 4, the elliptically expanding multi-segment intussuscepted tube hydraulic surgical retractor 400 can included a first inwardly folded sheath 410 that can extend from the first coupling 406, approximately 90 degrees in a clockwise direction, to a terminating end. A second inwardly folded sheath 412 that can extend from the second coupling 408, approximately 90 degrees in a counter-clockwise direction, to a terminating end that can be spaced by a gap (visible in FIG. 4, but not separately labeled) from the terminating end of the first inwardly folded sheath 410. The lower telescoping tube segment can have a mirror of the first inwardly folded sheath 410 and of the second inwardly folded sheath 412.

When fluid is introduced at pressure into the elliptically expanding multi-segment intussuscepted tube hydraulic surgical retractor 400, four telescoping and unfolding actions can occur. One can be a telescoping of the sheathed left portion 404L out of the first inwardly folded sheath 410. Included in the telescoping can be an unfolding of the first inwardly folded sheath 410. A second telescoping and unfolding action can be a telescoping of the sheathed right portion 404R out of the second inwardly folded sheath 412. Included in that telescoping can be an unfolding of the second inwardly folded sheath 412. The remaining two telescoping and unfolding actions can be performed by the mirror of the first inwardly folded sheath 410 and of the second inwardly folded sheath 412 that are associated with the lower telescoping tube segment.

Referring to FIG. 4, a result of the above-described four telescoping and unfolding actions can be an elliptical expansion, in directions labeled "Lateral Expansion" to an elliptical outer perimeter "OP." The expansion can exert lateral forces labeled "FL". When the elliptical outer perimeter OP is reached, the elliptically expanding multi-segment intussuscepted tube hydraulic surgical retractor 400 can have a lateral diameter D6, along the X or horizontal axis that is significantly larger than the starting or rest state diameter (visible in FIG. 4, but not separately labeled). The vertical or Y-axis diameter, in contrast, may not expand significantly.

The elliptically expanding multi-segment intussuscepted tube hydraulic surgical retractor 400, as described, expands symmetrically along the X-axis and along the Y-axis. The symmetrical expansion results from the symmetrical configuration of the upper telescoping tube segment 402 and the mirror configuration of the lower telescoping tube segment.

In certain applications, though, an asymmetrical retraction can be preferred.

Figure 5:
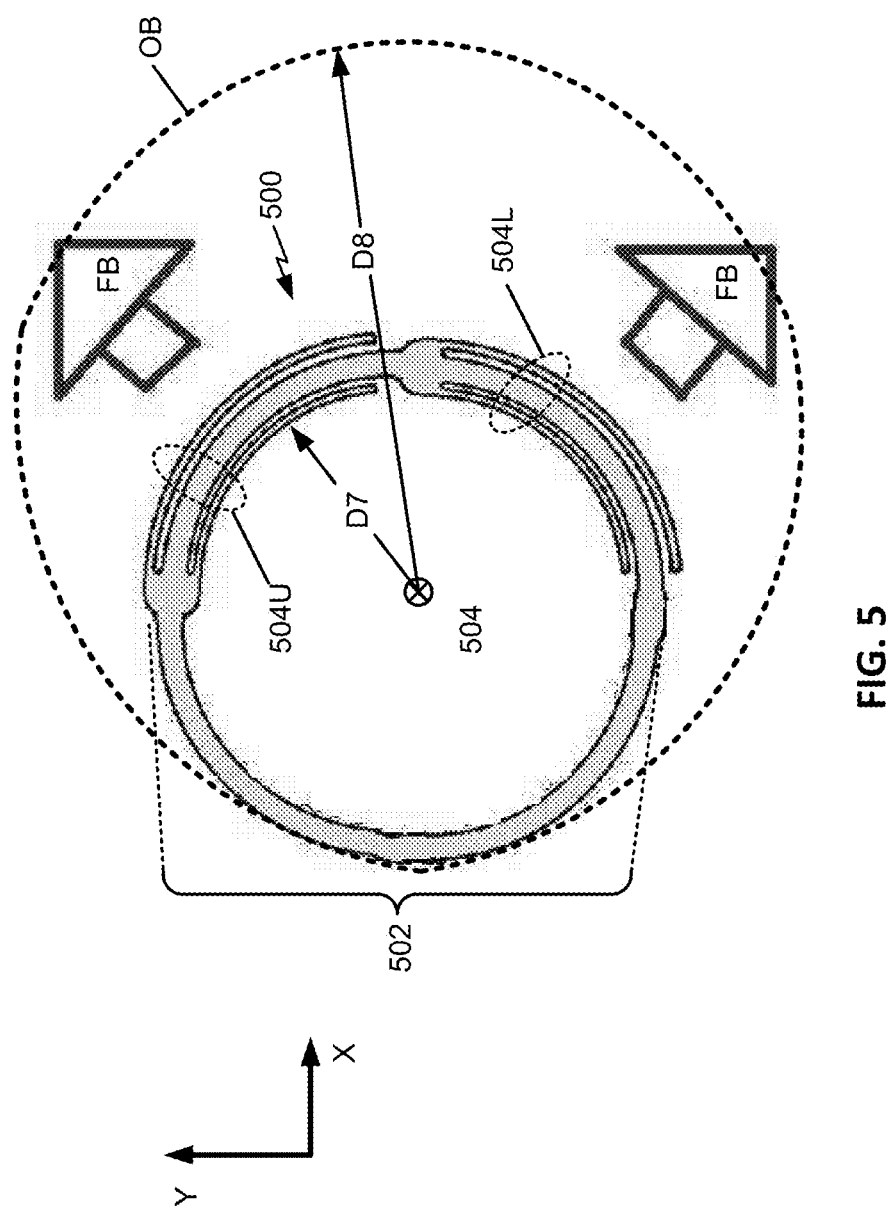
FIG. 5 illustrates a rest mode, and a diagrammed expansion, of one example directionally biased elliptically expanding multi-segment intussuscepted tube hydraulic surgical retractor according to one or more aspects.

FIG. 5 illustrates a rest mode, and a diagrammed expansion, of one example directionally biased expanding multi-segment intussuscepted tube hydraulic surgical retractor 500 according to one or more aspects.

Referring to FIG. 5, the directionally biased expanding multi-segment intussuscepted tube hydraulic surgical retractor 500 can include a non-segmented left loop 502, and segmented right loop formed of an upper right quadrant telescoping tube arc segment 504U and a lower right quadrant telescoping tube arc segment 504L. In an aspect, the upper right quadrant telescoping tube arc segment 504U and the lower right quadrant telescoping tube arc segment 504L can be structured substantially identical to the intussuscepted tube arc segments 102 described in reference to FIGS. 1A and 1B.

Referring to FIG. 5, the directionally biased expanding multi-segment intussuscepted tube hydraulic surgical retractor 500, in rest mode, can be approximately circular, with an approximate or average radius D7. When fluid is introduced at pressure into the directionally biased multi-segment intussuscepted tube hydraulic surgical retractor 500, two telescoping and unfolding actions can occur. Each can be according to the telescoping and unfolding actions of the intussuscepted tube arc segments 102 described in reference to FIGS. 1A and 1B. A result of the two telescoping and unfolding actions can be a directionally biased expansion, in directions labeled "FB." When the elliptical outer perimeter OB is reached, the elliptically expanding multi-segment intussuscepted tube hydraulic surgical retractor 400 can have a directionally biased bulb or bulge (visible in FIG. 5 but not separately labeled) having a "radius" D8, measured from the same center as the starting radius D7.

The direction of the directional bias of the directionally biased expanding multi-segment intussuscepted tube hydraulic surgical retractor 500 is established by the arrangement of the non-segmented left loop 502, and of the segmented right loop formed of an upper right quadrant telescoping tube arc segment 504U and lower right quadrant telescoping tube arc segment 504L. The particular direction of the directional bias illustrated in FIG. 5 is only for purposes of example. Other bias directions can be provided, for example, by modifying the quantity and arrangement of the non-segmented portions, and of the telescoping tube arc segments.

Figure 6:
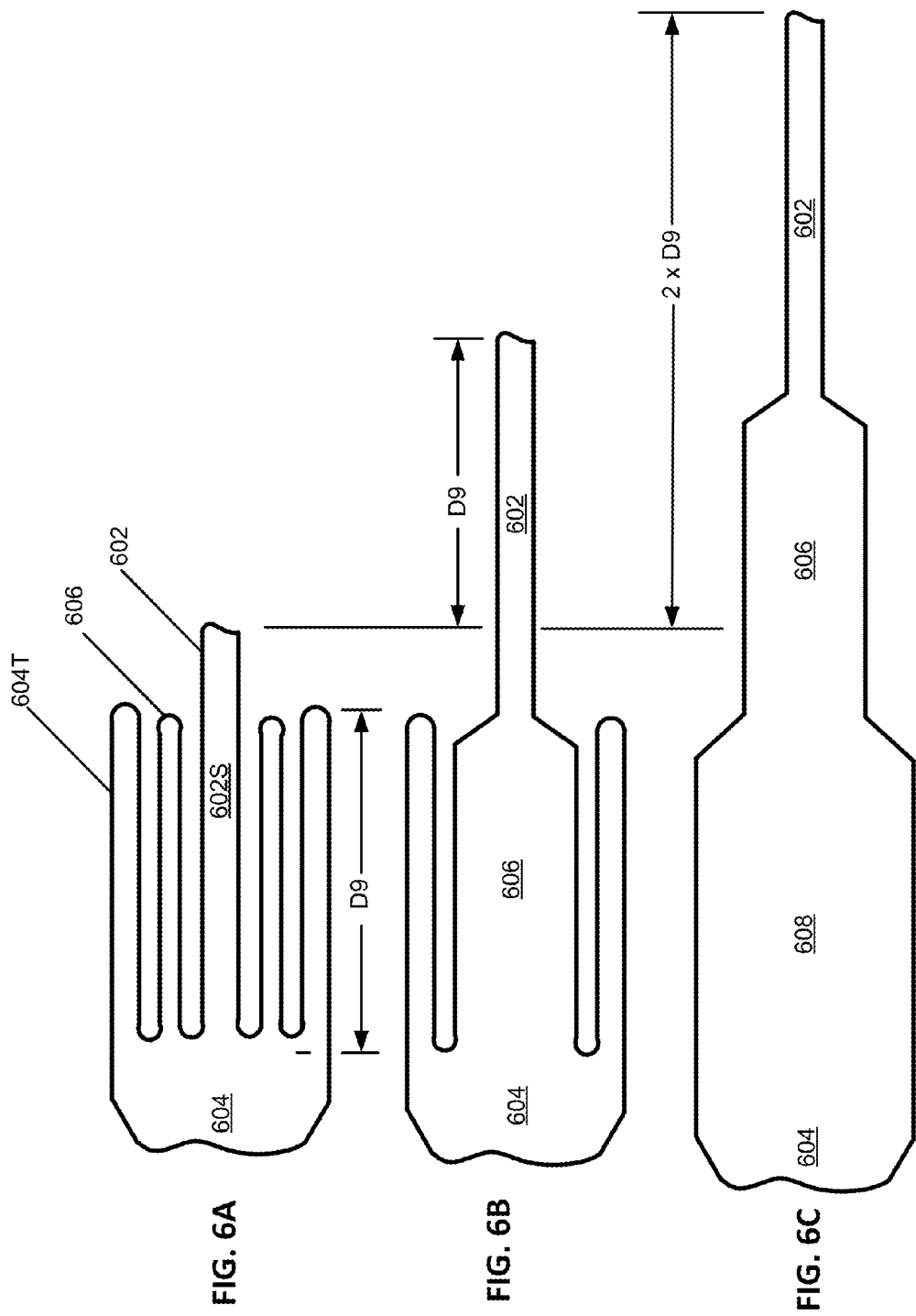
FIGS. 6A, 6B and 6C illustrate, respectively, a rest mode, a single extension mode, and a double extension mode of one exemplary two-time intussuscepted tube segment according to one or more aspects.

FIGS. 6A, 6B and 6C illustrate, respectively, a rest mode, a single extension mode, and a double extension mode of one exemplary two-time intussuscepted tube segment 600 according to one or more aspects, a telescoping core tube 602.

Referring to FIG. 6A, in rest mode a sheathed portion 602A (marked by right-diagonal hash lines) of the telescoping core tube 602 is at a position that appears pulled into or taken into, and surrounded by an inwardly folded inner sheathing portion 604S of a coupling tube 604. The sheathed portion 602A has a length D9. To simulate pressure that would result from importation of fluid into a closed loop that included the two-time intussuscepted tube segment 600 an artificial obstruction BX is placed at the distal end (visible in FIGS. 6A-6C) but not separately labeled) of the telescoping core tube 602. The FIG. 3 hand pump 302 and valve 308, or alternate means can be used to introduce fluid pressure into the two-time intussuscepted tube segment 600.

Referring to FIG. 6B, upon a particular pressure level of the imported fluid, the telescoping core tube 602 has telescoped, by the distance D8 in the direction of the fluid pressure. The telescoping caused the FIG. 6A sheathed portion 602A to also telescope out, to transform the inwardly folded inner sheathing portion 604S into a sheathed inner coupling tube 606. The sheathed inner coupling tube 606 is at a position that appears pulled into or taken into, and surrounded by an inwardly folded outer sheathing portion 604T of the coupling tube 604.

Referring to FIG. 6C, upon another, higher particular pressure level of the imported fluid, the sheathed inner coupling tube 606 telescopes in the direction of the fluid pressure. The telescoping of the FIG. 6B sheathed inner coupling tube 606 transforms the inwardly folded outer sheathing portion 604T of the coupling tube 604 into an intermediate coupling tube 608. For this example, since the length of the inwardly folded outer sheathing portion 604T is D8, the distance the sheathed inner coupling tube 606 telescopes to reach the FIG. 6C double extended mode is also D8. Therefore, the total telescoped extension of the two-time intussuscepted tube segment 600 according to one or more aspects, is quadruple D9.

Figure 7:
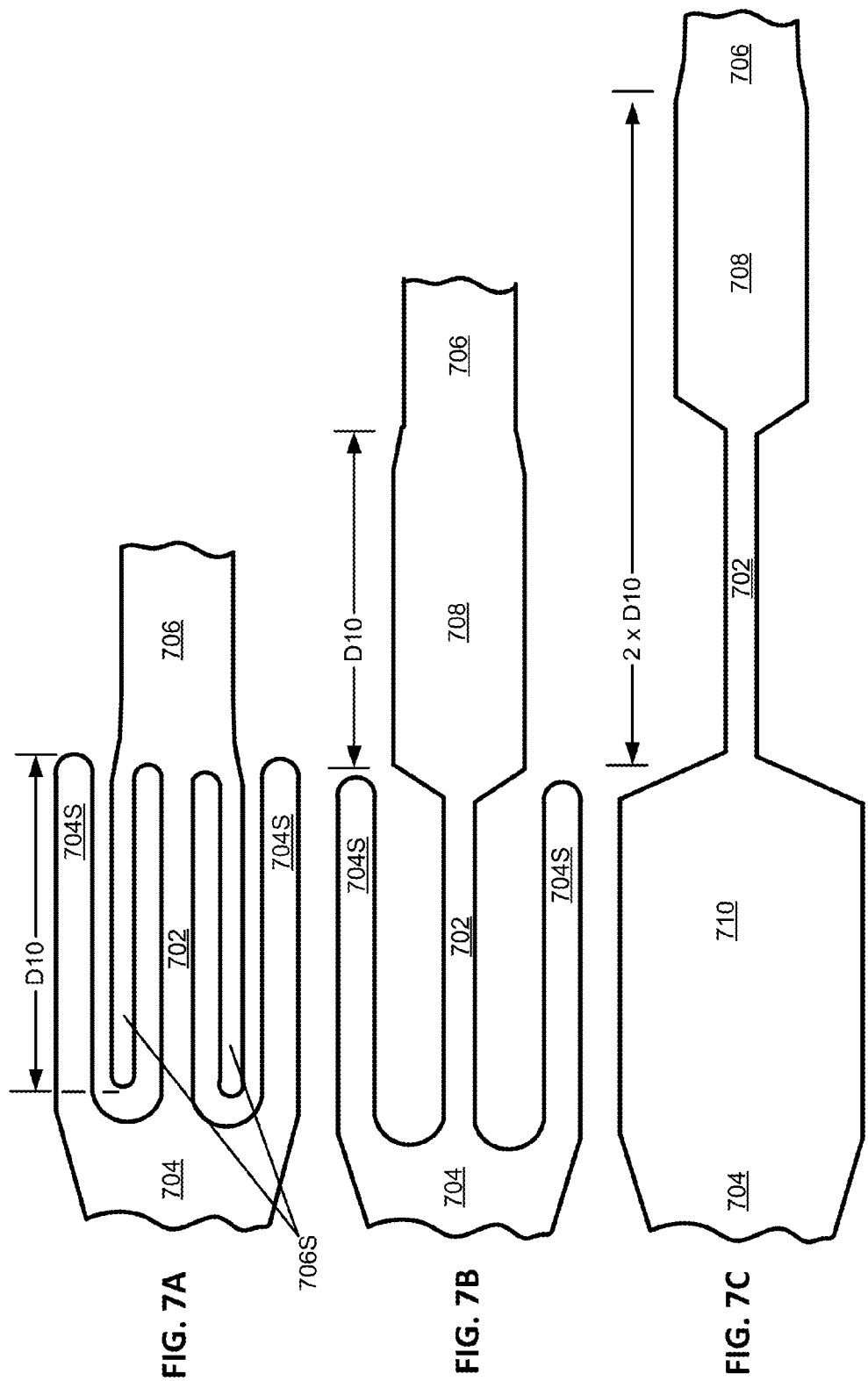
FIGS. 7A, 7B and 7C illustrate, respectively, a rest mode, a single extension mode, and a double extension mode of another exemplary two-time intussuscepted tube segment according to one or more aspects.

FIGS. 7A, 7B and 7C illustrate, respectively, a rest mode, a single extension mode, and a double extension mode of another exemplary two-time intussuscepted tube segment 700 according to one or more aspects.

Referring to FIG. 7A, in rest mode a coupling core tube 702 can connect a first tube 704 to a second tube 706. The coupling core tube 702 can be surrounded by an inwardly folded sheathing portion 706S of the second tube 706. The inwardly folded sheathing portion 706S of the second tube 704, in turn, can be taken into and surrounded by an inwardly folded sheathing portion 704S of the first tube 704. The inwardly folded sheathing portion 706S of the second tube 706, and inwardly folded sheathing portion 706S of the second tube 704 can therefore function, respectively, as an inner sheath and an outer sheath for the coupling core tube 702. In the example illustrated by FIG. 7A, the inwardly folded sheathing portion 706S of the second tube 706, and the inwardly folded sheathing portion 704S of the first tube 704 can have the same, or approximately the same length, D10. Accordingly, as will be understood from FIGS. 7B and 7C, the two-time intussuscepted tube segment 700 can extend a total of quadruple D10.

To simulate pressure that would result from importation of fluid into a closed loop that included the two-time intussuscepted tube segment 700 an artificial obstruction BZ is placed at the distal end (visible in FIGS. 7A-7C) but not separately labeled) of the second tube 704. The FIG. 3 hand pump 302 and valve 308, or alternate means can be used to introduce fluid pressure into the two-time intussuscepted tube segment 700.

Referring to FIG. 7B, upon a particular pressure level of the imported fluid, the inwardly folded sheathing portion 706S of the second tube 706 can unfold to remove the effective inner sheath from the coupling core tube 702. Upon completion of the unsheathing, the inwardly folded sheathing portion 706S is transformed into a telescoped coupling tube 708. The coupling core tube 702 is still sheathed by its effective outer sheath, which is the inwardly folded sheathing portion 704S of the first tube 704. Upon reaching the first extended mode 700B, the two-time intussuscepted tube segment 700, the first tube 704 and the second tube 706 extend apart by the distance D9, which was the length of the inwardly folded sheathing portion 706S of the second tube 706 in the rest state 700A.

Referring to FIG. 7C, upon another, higher particular pressure level of the imported fluid, the inwardly folded sheathing portion 704S of the first tube 704 (i.e., the effective outer sheath of the coupling tube 702) unfolds and the coupling core tube 702 telescopes in the direction of the fluid pressure. These unfolding and telescoping operations transform the inwardly folded sheathing portion 704S of the first tube 704 into a telescoped coupling tube 710. For this example, since the length of the inwardly folded sheathing portion 704S of the first tube 704 is D9, the length of the telescoped coupling tube 710 is approximately D9. Therefore, the total telescoped extension of the two-time intussuscepted tube segment 700 according to one or more aspects, is quadruple D9.

Figure 8:
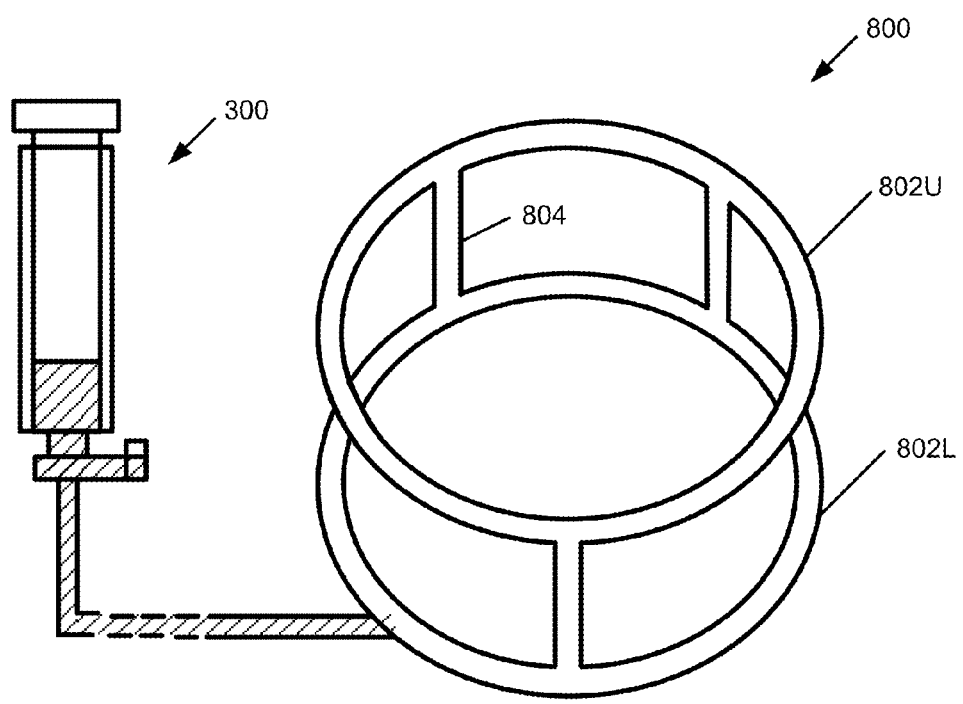
FIG. 8 illustrates one example of a scaffolding implementation of one exemplary intussuscepted tube hydraulic surgical retractor according to one or more aspects.

FIG. 8 illustrates a scaffold structured multi-segment intussuscepted tube hydraulic surgical retractor 800 according to various aspects. The scaffold structured multi-segment intussuscepted tube hydraulic surgical retractor 800 can include an upper multi-segment intussuscepted tube hydraulic surgical retractor 802U, and a lower multi-segment intussuscepted tube hydraulic surgical retractor 802L, connected through at least three bracings 804. In an aspect, the bracings 804 can be intussuscepted tube bracings, structured (but not necessarily arced) such as the intussuscepted tube arc segments 102 described above in reference to FIGS. 1A-1B. In one implementation, a hand pump such as the hand pump 302 can connect to one of the upper multi-segment intussuscepted tube hydraulic surgical retractor 802U and lower multi-segment intussuscepted tube hydraulic surgical retractor 802L, and fluid may flow through the bracings 804. In one aspect, the upper multi-segment intussuscepted tube hydraulic surgical retractor 802U and the lower multi-segment intussuscepted tube hydraulic surgical retractor 802L can be configured such as the multi-segment intussuscepted tube hydraulic surgical retractor 100. Accordingly, upon the hand pump 302 or another source urging fluid into the scaffold structured multi-segment intussuscepted tube hydraulic surgical retractor 800, the upper multi-segment intussuscepted tube hydraulic surgical retractor 802U and lower multi-segment intussuscepted tube hydraulic surgical retractor 802L can each expand, such as described in reference to FIG. 1B. In addition, the bracings 804, being implemented as intussuscepted tube segments, can telescope. This implementation can provide a scaffold structured multi-segment intussuscepted tube hydraulic surgical retractor 800 that expands uniformly outwards, therefore causing the surgical site to retract. In one alternative implementation, one or both of the upper multi-segment intussuscepted tube hydraulic surgical retractor 802U and lower multi-segment intussuscepted tube hydraulic surgical retractor 802L can be configured such as the FIG. 4 elliptically expanding multi-segment intussuscepted tube hydraulic surgical retractor 400, or according to the FIG. 5 directionally biased expanding multi-segment intussuscepted tube hydraulic surgical retractor 500. In one or more implementations of the scaffold structured multi-segment intussuscepted tube hydraulic surgical retractor 800, the bracings or bracing tubes 804 can form an operational area by holding tissues, for example bowels, apart.

Figure 9:
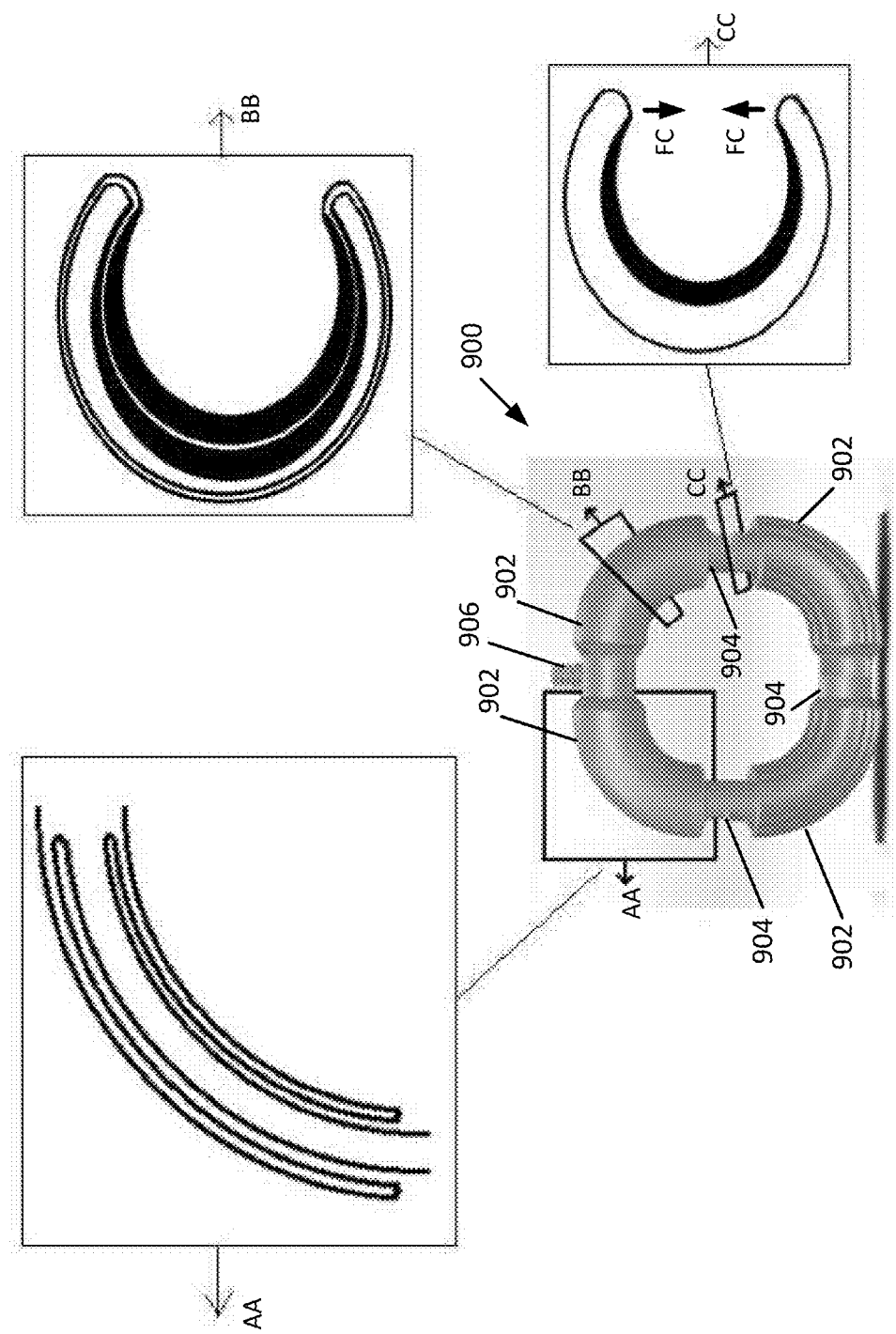
FIG. 9 shows a simulation model, illustrating exemplary structure on cut plane projections, of one multi-segment intussuscepted tube surgical apparatus, configured with hydraulic retractor and clamping features, according to one or more aspects.

FIG. 9 is a simulated top projection view, further illustrating exemplary structure on cut plane projections, of one multi-segment intussuscepted C-tube surgical retractor/clamp 900, configured with hydraulic retractor and clamping features according to one or more aspects.

Referring to FIG. 9, the multi-segment intussuscepted C-tube surgical retractor/clamp 900 can include four intussuscepted C-tube segments 902 connected in a loop arrangement by four C-tube couplings 904. Cut plane AA illustrates example internal structure of a representative one of the intussuscepted C-tube segments 902 and of a portion of a corresponding one of the C-tube couplings 904. Cut plane BB illustrates one example cross-sectional structure of one of the intussuscepted C-tube segments 902. Cut plane CC illustrates one example cross-sectional structure of one of the C-tube couplings 904. In an aspect, a controlled pressure fluid source, for example, the hand pump 302, feed tube 304 and valve 308 described above, can couple to the fluid ingress/egress port 906. Upon fluid being urged into the fluid port 906 the four intussuscepted C-tube segments 902 can telescope as described, for example, in reference to one or more of FIGS. 1A, 1B, 2A and 2B. The telescoping can provide retracting operations, such as described above in reference to one or more of FIGS. 1A, 1B, 2A, 2B, 4 and 5.

Figures 10A, 10B:
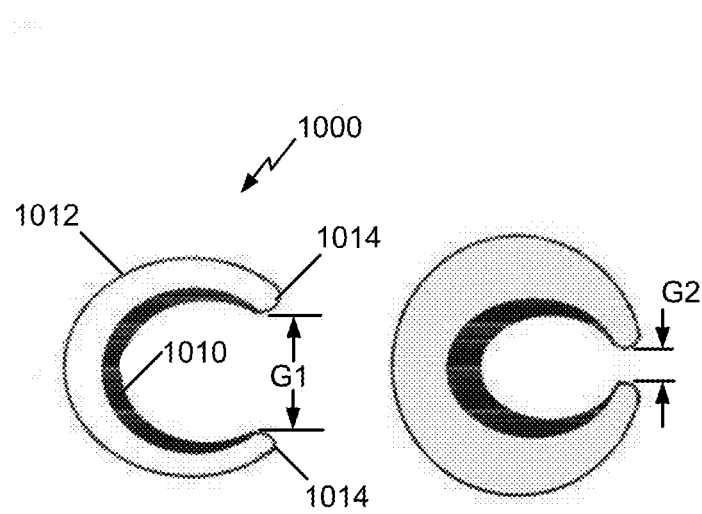
FIGS. 10A and 10B are cross-sectional illustrations of one C-shaped hydraulic clamping retractor according to one implementation, in rest mode (FIG. 9A) and in fully expanded mode (FIG. 10B).

Referring to FIG. 9 cut planes BB and CC, in an aspect, the C-shaped internal structure of the four intussuscepted C-tube segments 902 and four C-tube couplings 904 can provide, additional to the telescoping and retracting operations described above, a clamping operation. For example, referring to cut planes BB and CC, the fluid pressure can exert a clamping force in the FC directions. D FIGS. 10A and 10B illustrate a C-shaped retractor 1000 according to one or more aspects. The C-shaped retractor 1000 can include an inner C-shaped layer 1010 and an outer C-shaped layer 1012. The inner C-shaped layer 1010 can be thicker than the outer C-shaped layer 1012, as seen in FIG. 10A. Upon expansion of the retractor 1000, the difference in thicknesses can cause the inner C-shaped layer 1010 to expand at slower rate than the outer C-shaped layer 1012, as shown in FIG. 10B, therefore, causing the two ends of the retractor to get closer to each other, closing the gap. Therefore, the expanded retractor 1000 may be used to hold the wound and stop further blooding.

Figure 11:
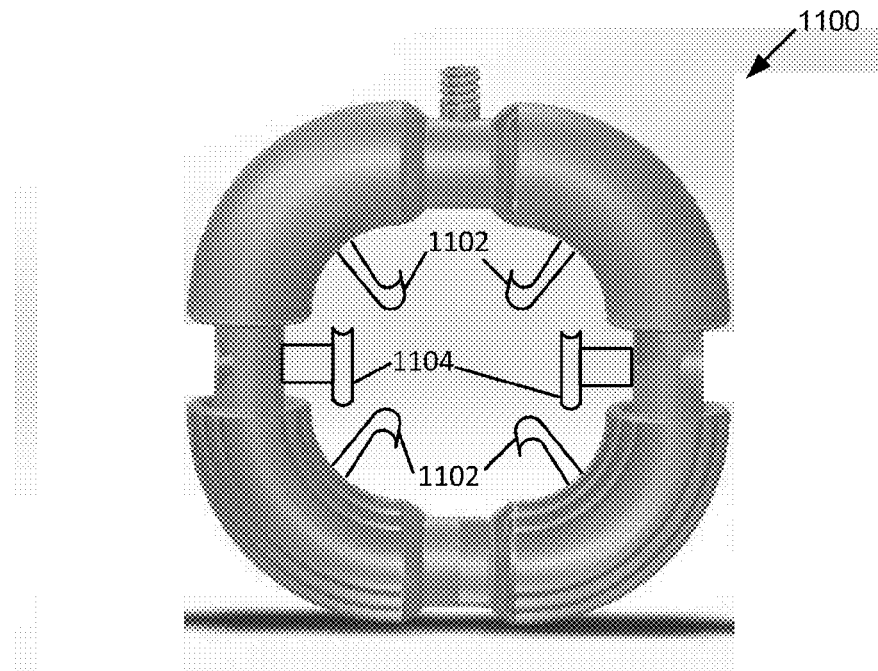
FIG. 11 illustrates a projection view of one exemplary intussuscepted tube hydraulically actuated surgical retractor, with example pull structures, according to one or more aspects.

FIG. 11 illustrates a projection view of one exemplary intussuscepted tube hydraulically actuated surgical retractor 1100, with example pull structures according to one or more aspects. Referring to FIG. 11, example pull structures can include hook-type retractors 1102. Other than attachment to the intussuscepted tube segments (visible in FIG. 11, but not separately numbered), the hook-type retractors 1102 can be in accordance with conventional hook-type retractor structure. In an aspect, either alternative to or additional to the hook-type retractors 1102, the intussuscepted tube hydraulically actuated surgical retractor 1100 can include curved contact type spreading retractors 1104.

Figure 12:
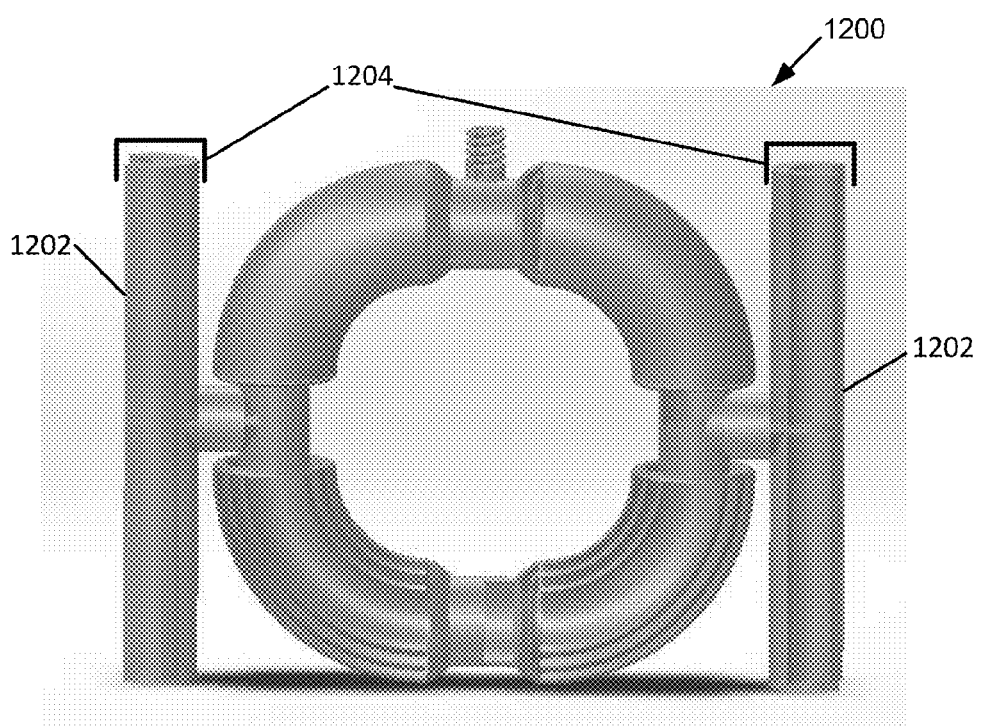
FIG. 12 illustrates a projection view of one exemplary intussuscepted tube hydraulically actuated retractor with example push members according to one or more aspects.

FIG. 12 illustrates a projection view of one exemplary intussuscepted tube hydraulically actuated retractor 1200, with engagement members 1202. The engagement members 1202 can be engaged, for example, with conventional retractors 1204. Upon fluid being urged into fluid port 1206, intussuscepted segments (visible in FIG. 12, but not separately numbered) can telescope such as described above in reference to one or more of FIGS. 1A, 1B, 2A, 2B, 4 and 5, in turn urging the conventional retractors 1204 to push tissue.

The separation of various components in the examples described above should not be understood as requiring such separation in all examples, and it should be understood that the described components and systems can generally be integrated together in a single packaged into multiple systems.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus the following claims are hereby incorporated into the Detailed Description, with each claim standing on its own as a separately claimed subject matter.

What is claimed is:

1. A fluidly expandable surgical retractor, comprising:
   a segmented annular tube, the segmented annular tube including a flexible material and a telescoping intussuscepted tube arc segment;
   a feed tube in fluid communication with an interior of the segmented annular tube;
   a pump, having an output coupled to the feed tube, and having an input configured to receive a fluid; and
   a flow control valve, configured to selectively increase and decrease a flow of the fluid through the feed tube, into and out of the segmented annular tube,
   wherein
   the telescoping intussuscepted tube arc segment includes a core tube and an outer tube, and is configured to expand and retract in association with increase and decrease, respectively, of the flow of the fluid through the feed tube, wherein,
      to retract includes the outer tube forming, in response to a pressure of the fluid through the feed tube being less than a first pressure, an inwardly folded sheathing portion that surrounds a sheathed telescoping portion of the core tube, and
      to expand includes the outer tube unfolding, in response to the pressure increasing from the first pressure toward a second pressure, the inwardly folded sheathing portion and telescoping the sheathed telescoping portion of the core tube.

2. The fluidly expandable surgical retractor of claim 1, wherein the flow control valve is a manually actuated valve.

3. The fluidly expandable surgical retractor of claim 1, wherein
   the outer tube forming the inwardly folded sheathing portion that surrounds the sheathed telescoping portion of the core tube is configured as a resting mode, and
   the telescoping intussuscepted tube arc segment is further configured to expand to a fully expanded mode in response to the fluid pressure being above the second pressure.

4. The fluidly expandable surgical retractor of claim 3, wherein, in the resting mode, the telescoping intussuscepted tube arc segment includes the sheathed telescoping portion of the core tube being pulled into and surrounded by the inwardly folded sheathing portion of the outer tube.

5. The fluidly expandable surgical retractor of claim 4, wherein:
   the outer tube includes an intermediate coupling tube and an inner coupling tube, and the inner coupling tube connects to the core tube, and
   to expand and contract includes,
      in association with a resting state pressure of the fluid, a portion of the inner coupling tube folds to form an inner inwardly folded sheathing portion that surrounds the sheathed telescoping portion of the core tube, and a portion of the intermediate coupling tube folds to form an outer inwardly folded sheathing portion that surrounds the inner inwardly folded sheathing portion, and
      in association with an increase in the pressure of the fluid from the resting state pressure to a particular pressure, the sheathed telescoping portion of the core tube telescopes out, and the inner inwardly folded inner sheathing portion telescopes out and forms a sheathed inner coupling tube that is surrounded by the inwardly folded outer sheathing portion.

6. The fluidly expandable surgical retractor of claim 5, wherein,
   to expand and contract further includes,
      in response to an increase in the pressure of the fluid from the particular first pressure to another pressure, the inwardly folded outer sheathing portion unfolds and telescopes the sheathed inner coupling tube and further telescopes the core tube.

7. The fluidly expandable surgical retractor of claim 1, wherein:

the inwardly folded sheathing portion of the outer tube has a length, and the inwardly folded sheathing portion of the outer tube unfolds and telescopes the core tube, in a direction corresponding to a direction of the fluid pressure, to a distance approximately thrice the length of the inwardly folded sheathing portion in the resting mode.

8. The fluidly expandable surgical retractor of claim 1, wherein:

the telescoping intussuscepted tube arc segment is an upper telescoping intussuscepted tube arc segment, the inwardly folded sheathing portion is a first inwardly folded sheathing portion, and the annular tube further comprises a lower telescoping intussuscepted tube arc segment, in fluid connection through a first coupling and a second coupling.

9. The fluidly expandable surgical retractor of claim 8, wherein the upper telescoping intussuscepted tube arc segment includes:

an upper core tube, wherein the upper core tube includes an unsheathed center portion, a sheathed left portion, and a sheathed right portion;

a first inwardly folded sheath that extends from the first coupling approximately 90 degrees in a clockwise direction, to a terminating end;

a second inwardly folded sheath that can extends from the second coupling, approximately 90 degrees in a counter-clockwise direction, to a terminating end that is spaced by a gap from the terminating end of the first inwardly folded sheath.

10. The fluidly expandable surgical retractor of claim 1, wherein the segmented annular tube comprises a plurality of telescoping intussuscepted tube arc segments, wherein each telescoping intussuscepted tube arc segment includes a corresponding core tube having a corresponding sheathed telescoping portion, pulled into and surrounded by a corresponding inwardly folded sheathing portion of a corresponding outer tube, wherein, in response to an increase in the pressure of the fluid from less than the first pressure to greater than the second pressure, the corresponding inwardly folded sheathing portion of each intussuscepted tube segment unfolds and telescopes the corresponding core tube.

11. The fluidly expandable surgical retractor of claim 10, wherein the segmented annular tube is approximately circular in the resting mode, and wherein the plurality of telescoping intussuscepted tube arc segments is arranged such that, in response to the corresponding inwardly folded sheathing portion of each telescoping intussuscepted tube arc segment unfolding and telescoping the core tube, the segmented annular tube expands radially, at a substantially uniform rate.

12. The fluidly expandable surgical retractor of claim 10, wherein the segmented annular tube is approximately circular in the resting mode, and wherein the plurality of telescoping intussuscepted tube arc segments is arranged such that, in response to the corresponding inwardly folded sheathing portion of each telescoping intussuscepted tube arc segment unfolding and telescoping the core tube, the segmented annular tube expands to an elliptical perimeter.

13. The fluidly expandable surgical retractor of claim 10, wherein the plurality of telescoping intussuscepted tube arc segments is arranged such that, in response to the corresponding inwardly folded sheathing portion of each telescoping intussuscepted tube arc segment unfolding and telescoping the core tube, the segmented annular tube expands in a directionally biased manner.

14. The fluidly expandable surgical retractor of claim 1, further comprising a light source.

15. The fluidly expandable surgical retractor of claim 1, further comprising a power source.

16. The fluidly expandable surgical retractor of claim 1, wherein the pump is a hydraulic pump.

17. The fluidly expandable surgical retractor of claim 1, wherein the segmented annular tube is a first segmented tube, wherein the fluidly expandable surgical retractor further comprises:

a second segmented annular tube, comprising a flexible material and arranged above or below the first segmented annular tube, the second segmented annular tube comprising a flexible material and including another intussuscepted tube segment; and a plurality of bracings, each of the bracings being a hollow tube or an intussuscepted tube, and each of the bracings extending between and providing a fluid communication between the first segmented annular tube and the second segmented annular tube.

18. The fluidly expandable surgical retractor of claim 17, wherein the first segmented annular tube and the second segmented annular tube, and the plurality of bracings are configured as a scaffolding that, upon an increase in flow rate of the fluid through the feed tube, expands outwardly.

19. A method for retracting tissue, comprising:

placing into a surgical site a segmented annular tube, comprising a flexible material and including a telescoping intussuscepted tube arc segment, the telescoping intussuscepted tube arc segment including a core tube having a sheathed telescoping portion, configured as pulled into and surrounded by an inwardly folded sheathing portion of an outer tube; and importing a fluid into the segmented annular tube, at a pressure that causes the inwardly folded sheathing portion of the outer tube to unfold and telescope the core tube to expand the segmented annular tube.

* * * * *